United States Patent [19]
Breton et al.

[11] Patent Number: 6,019,967
[45] Date of Patent: Feb. 1, 2000

[54] THERAPEUTIC/COSMETIC COMPOSITIONS COMPRISING CGRP ANTAGONISTS FOR TREATING SENSITIVE HUMAN SKIN

[75] Inventors: Lionel Breton, Versailles; Olivier De Lacharriere, Paris, both of France

[73] Assignee: Societe L'Oreal S.A., Paris, France

[21] Appl. No.: 08/592,529

[22] Filed: Jan. 26, 1996

[30] Foreign Application Priority Data

Jan. 26, 1995 [FR] France ................................ 95 00900

[51] Int. Cl.[7] ................................................. A61K 39/395
[52] U.S. Cl. ..................... 424/130.1; 424/401; 424/70.1; 424/47; 424/489; 514/2; 514/844; 514/846; 514/937; 530/387.1; 530/300
[58] Field of Search ................................. 424/130.1, 401, 424/70.1, 47, 489; 514/844, 846, 937, 944, 945, 2; 530/387.1, 300

[56] References Cited

U.S. PATENT DOCUMENTS

| | | | |
|---|---|---|---|
| 4,777,034 | 10/1988 | Olivier et al. | 424/65 |
| 5,013,545 | 5/1991 | Blackman et al. | 424/81 |
| 5,420,106 | 5/1995 | Pazab et al. | 514/2 |
| 5,520,918 | 5/1996 | Smith | 424/401 |
| 5,543,148 | 8/1996 | Lapidus | 424/401 |

FOREIGN PATENT DOCUMENTS

93/21911  11/1993  WIPO .

OTHER PUBLICATIONS

Buckley, TL et al. Neuroscience 48: 963–968, 1992.
Escott, K J. et al. British J. Pharmacol. 110(2):772–776, 1993.
Hughes, Sr. et al. British J. Pharmacol. 104 (3):738–742, 1991.
Singh, P. et al. 1994. Critical Reviews in Theurapeutic Drug Carrier Systems 11:161–213.

*Primary Examiner*—Paula K. Hutzell
*Assistant Examiner*—Minh Tam Davis
*Attorney, Agent, or Firm*—Burns, Doane, Swecker & Mathis, L.L.P.

[57] ABSTRACT

Topically applicable pharmaceutical/dermatological/cosmetic compositions well suited for the therapeutic treatment or care of sensitive human skin, hair, mucous membranes, nails and/or the scalp, in particular for reducing or avoiding the skin-irritant side effects of a variety of bioactive agents, for example the α-hydroxy acids, comprise a therapeutically/cosmetically effective amount of at least one calcitonin gene related peptide ("CGRP") antagonist, e.g., CGRP 8-37 or an anti-CGRP antibody.

13 Claims, No Drawings

THERAPEUTIC/COSMETIC COMPOSITIONS COMPRISING CGRP ANTAGONISTS FOR TREATING SENSITIVE HUMAN SKIN

BACKGROUND OF THE INVENTION

1. Technical Field of the Invention

The present invention relates to the formulation of an antagonist of CGRP (peptide derived from the calcitonin gene: Calcitonin Gene Related Peptide, or "CGRP") into topically applicable cosmetic/pharmaceutical/ dermatological compositions, for the treatment of sensitive skin-types, as well as to cosmetic compositions containing a CGRP antagonist for reducing or eliminating the irritant effects elicited by certain active agents, and especially by certain bioactive agents conventionally employed in the cosmetics, pharmaceutical or dermatological field.

2. Description of the Prior Art

It is known to this art that certain skin-types are more sensitive than others. The symptoms of sensitive skin-types were heretofore poorly characterized and the problem of these skin-types was, as a result, poorly defined; the exact mechanism involved in the sensitivity—nonallergic cutaneous hyperreactivity—of the skin, was unknown. In certain quarters it was believed that a sensitive skin was a skin which reacted to cosmetic products, while others believed that it concerned a skin which reacted to a variety of external factors, not necessarily associated with cosmetic products.

Certain tests have been conducted in attempting to define sensitive skin-types, for example tests using lactic acid and DMSO which are known to be irritant substances: see, for example, the article by K. Lammintausta et al, *Dermatoses*, 36, pages 45–49 (1988); and the article by T. Agner and J. Serup, *Clinical and Experimental Dermatology*, 14, pages 214–217 (1989). However, these tests did not make it possible to characterize sensitive skin-types.

Moreover, sensitive skin-types were likened to allergic skin-types.

Taking account of the ignorance of the characteristics of sensitive skin-types, it was hitherto very difficult to treat them and they were treated indirectly, for example by limiting, in the cosmetic compositions, active species eliciting an irritant effect, such as surfactants, preservatives or perfumes, as well as certain otherwise bioactive agents.

The assignee hereof has now conducted many clinical tests and has been able to determine the symptoms associated with sensitive skin-types. These symptoms are, in particular, subjective signs, which are essentially dysaesthesic sensations. By the term "dysaesthesic sensations" are intended more or less painful sensations experienced in an area of the skin, such as stinging, tingling, itching or pruritus, burning, inflammation, discomfort, pulling, etc.

The assignee hereof has also been able to demonstrate that a sensitive skin-type is not an allergic skin-type. Indeed, an allergic skin-type is a skin-type which reacts to an external agent, an allergen, which triggers an allergic reaction. This is an immunological process which takes place only when an allergen is present and which affects only sensitized individuals. To the contrary, the essential characteristic of sensitive skin, according to the assignee hereof, is a mechanism of response to external factors, which may be the case for any individual, even if the individuals said to have sensitive skin react faster thereto than the other individuals. This is a nonspecific mechanism and not an immunological one.

It has now been determined that sensitive skin-types can be divided into two major clinical forms; irritable and/or reactive skin-types and intolerant skin-types.

An irritable and/or reactive skin-type is a skin-type which reacts by a pruritus, i.e., by itching, or by stinging, to various factors such as the environment, emotions, foods, the wind, rubbing, shaving, soap, surfactants, hard water having a high calcium concentration, temperature variations or wool. In general, these signs are associated with a dry skin with or without dartres, or with a skin which displays an erythema.

An intolerant skin-type is a skin-type which reacts, by sensations of inflammation, pulling, tingling and/or redness, to various factors such as the environment, emotions and foods. In general, these signs are associated with a hyperseborrhoeic or acneic skin-type with or without dartres, and with an erythema.

"Sensitive" scalps have a more unequivocal clinical semeiology: the sensations of pruritus and/or of stinging and/or of inflammation are essentially triggered by local factors such as rubbing, soap, surfactants, hard water with a high calcium concentration, shampoos or lotions. These sensations are also sometimes triggered by factors such as the environment, emotions and/or foods. Erythema and hyperseborrhoea of the scalp and the presence of dandruff are often associated with the above signs.

Moreover, in certain anatomical regions such as the major folds (groin, genital, axillary, popliteal, anal and submammary regions, and in the crook of the elbow) and the feet, sensitive skin is reflected in pruriginous sensations and/or dysaesthesic sensations (inflammation, stinging) associated in particular with sweat, rubbing, wool, surfactants, hard water with a high calcium concentration and/or temperature variations.

The assignee hereof has also now developed a test in order to determine whether or not a skin-type is sensitive. Indeed, after having carried out a multitude of tests for the purpose of defining sensitive skin, it has now surprisingly been found that there is a nexus between individuals with sensitive skin and those who react to a topical application of capsaicin.

The capsaicin test entails applying, to about 4 $cm^2$ of skin, 0.05 ml of a cream containing 0.075% of capsaicin and in noting the appearance of subjective signs induced by this application, such as stinging, burning and itching. In individuals having sensitive skin, these signs appear between 3 and 20 minutes after application and are succeeded by the appearance of an erythema which begins at the edge of the zone of application.

Hitherto, capsaicin was used as a medicinal active agent, in particular for treating zona pains. Capsaicin induces a release of neuropeptides from sensitive nerve fibers, and in particular of CGRP which originates from epidermal and dermal nerve endings. It has been observed that the physiopathological pattern common to the conditions of sensitive skin-types was associated with a marked ability to release neuropeptides, and more particularly CGRP, into the skin. The dysaesthesic manifestations which are induced by their release are referred to as "neurogenic."

CGRP is a polypeptide chemical species produced and released by a nerve ending. CGRP is involved, in particular, in respiratory and inflammatory diseases, in allergic diseases and in certain dermatological diseases such as eczema or prurigo.

SUMMARY OF THE INVENTION

It has now been determined that one of the essential characteristics of sensitive skin-types is associated with the release of CGRP and, thus, that the use of CGRP antagonists could permit a preventive and/or curative effect to be obtained for sensitive skin-types induced by an exogenous factor, said factor being able to modify biophysical and biochemical skin parameters. Furthermore, one of particularities of sensitive skin is to answer to external irritation signals more quickly and easily than normal skins. In addition, each irritation of a sensitive skin begins by subjective signs (stinging, burning, etc.).

To treat sensitive skin-types, the CGRP antagonists are hereby employed. Indeed, it has now surprisingly been observed that the incorporation of a CGRP antagonist into a cosmetic, pharmaceutical or dermatological composition avoids the irritation of and/or dysaesthesic sensations in and/or pruritus of the skin and/or of the mucous membranes and/or erythema.

Briefly, the present invention features the formulation of at least one CGRP antagonist into compositions comprising a cosmetically, pharmaceutically or dermatologically acceptable medium, for treating sensitive skin-types, and for correcting neurogenic indications.

The present invention also features the use of at least one CGRP antagonist for preventing and/or combating skin irritations and/or dartres and/or erythema and/or inflammation sensations and/or dysaesthesia and/or pruritus of the skin and/or the mucous membranes.

DETAILED DESCRIPTION OF BEST MODE AND SPECIFIC/PREFERRED EMBODIMENTS OF THE INVENTION

More particularly according to the present invention, by a "cosmetically, pharmaceutically or dermatologically acceptable medium" is intended a medium which is compatible with the skin, the scalp, the nails and the mucous membranes. The composition containing the CGRP antagonist may be topically applied to the face, the neck, the hair and the nails, or any other area of body skin such as the major folds (axillary and submammary regions, the crook of the elbow, and the like).

By "CGRP antagonist" is intended any molecule, whether organic or inorganic, which is capable of effecting an inhibition of the receptor binding of the CGRP or of effecting an inhibition of the synthesis and/or release of CGRP by sensitive nerve fibers.

In order for a chemical species to be recognized as a CGRP antagonist, it must comply in particular with the following characteristic: have a pharmacological antagonist activity towards CGRP, i.e., induce a coherent pharmacological response, in particular, in one of the following tests:

(a) the antagonist species must reduce the vasodilation induced by capsaicin, and/or (b) the antagonist species must induce an inhibition of the release of CGRP by sensitive nerve fibers, and/or (c) the antagonist species must induce an inhibition of the contraction of the smooth muscle of the deferent canal induced by CGRP.

In addition, the antagonist must have an affinity for the CGRP receptors.

Hitherto, a correlation had not been established between CGRP and sensitive skin. The clinical signs of sensitive skin are essentially subjective: stinging, tingling, pruritus, pulling, inflammation and erythema. These signs are due to nonspecific external factors. The symptoms appear to be essentially localized on the face, the neck and the scalp, but may also appear on the entire body.

CGRP 8-37, an anti-CGRP antibody, is suitable for use according to this invention, for example, as a CGRP antagonist.

In the compositions according to the invention, the CGRP antagonist is preferably employed in an amount ranging from 0.000001% to 10% by weight relative to the total weight of the composition, and in particular in an amount ranging from 0.0001% to 5% by weight relative to the total weight of the composition.

The compositions of the invention may be formulated into all the pharmaceutical forms normally employed for topical application, in particular in the form of aqueous, aqueous/alcoholic or oily solutions or dispersions of the lotion or serum type, anhydrous or lipophilic gels, emulsions of liquid or semi-liquid consistency of the milk type, obtained by dispersion of a fatty phase in an aqueous phase (O/W) or conversely (W/O), or suspensions or emulsions of smooth, semi-solid or solid consistency of the cream or gel type, or alternatively microemulsions, microcapsules or microparticles, or vesicle dispersions of ionic and/or non-ionic type. These compositions are formulated according to conventional techniques.

They may also be used for the hair in the form of aqueous, alcoholic or aqueous/alcoholic solutions, or in the form of creams, gels, emulsions or mousses or alternatively in the form of aerosol compositions also containing a propellant under pressure.

The amounts of the various constituents of the compositions according to the invention are those conventionally used in the fields under consideration.

These compositions constitute, in particular, cleansing, protective, treatment or care creams for the face, for the hands, for the feet, for the major anatomical folds or for the body (for example day creams, night creams, makeup-removing creams, foundation creams and sun creams), makeup products such as fluid foundations, makeup-removing milks, body milks for care or protection, after-sun products in the form of milks, lotions, gels or mousses for skin care, such as cleansing or disinfecting lotions, antisun lotions, artificial tanning lotions, compositions for the bath, deodorizing compositions containing a bactericide, after-shave products (gels or lotions), hair-removing creams, compositions to counter insect bites, pain-relief compositions, compositions for treating acne, hyperseborrhoeic skin or seborrhoeic dermatitis, and compositions for treating certain skin diseases such as severe pruritus, rosacea, acne, leg ulcers, psoriasis, pustules and vibices.

The compositions according to the invention may also be formulated as solid preparations constituting cleansing bars or soaps.

The CGRP antagonist may also be incorporated into various haircare or hair treatment compositions, and in particular shampoos, which may be antiparasitic shampoos, hairsetting lotions, treating lotions, styling creams or gels, dye compositions (in particular oxidation dyes) optionally in the form of coloring shampoos, restructuring lotions for the hair, permanent-wave compositions (in particular compositions for the first stage of a permanent-waving operation), lotions or gels for combating hair loss, and the like.

The compositions of the invention may also be formulated for buccodental use, for example as a toothpaste or a mouthwash. In this event, the subject compositions may contain adjuvants and additives which are conventional for compositions for buccal use and, in particular, surfactants, thickeners, wetting agents, polishing agents such as silica, various active ingredients such as fluorides, in particular sodium fluoride, and optionally sweeteners such as sodium saccharinate.

When the compositions of the invention are formulated as an emulsion, the proportion of the fatty phase advantageously ranges from 5% to 80% by weight, and preferably from 5% to 50% by weight, relative to the total weight of the composition. The oils, the emulsifiers and the coemulsifiers employed in the compositions in emulsion form are selected from among those used conventionally in the cosmetics field. The emulsifier and the coemulsifier are advantageously present in the compositions at a proportion ranging from 0.3% to 30% by weight, and preferably from 0.5 to 20% by weight, relative to the total weight of the composition. The emulsion may also contain lipid vesicles.

When the compositions of the invention comprise an oily solution or gel, the fatty phase may constitute more than 90% of the total weight of the composition.

In known manner, the cosmetic compositions of the invention may also contain additives and adjuvants which are common in the cosmetics, pharmaceutical or dermatological field, such as hydrophilic or lipophilic gelling agents, hydrophilic or lipophilic active agents, preservatives, antioxidants, solvents, fragrances, fillers, screening agents, bactericides, odor absorbers and dyestuffs and colorants. The amounts of these various additives and adjuvants are those used conventionally in the cosmetics field and range, for example, from 0.01% to 10% of the total weight of the composition. Depending on their nature, these adjuvants may be introduced into the fatty phase, into the aqueous phase and/or into the lipid spherules.

Exemplary oils which are suitable for the compositions of the invention include mineral oils (liquid petrolatum), plant oils (liquid fraction of karite butter, sunflower oil), animal oils (perhydrosqualene), synthetic oils (Purcellin oil), silicone oils (cyclomethicone) and fluoro oils (perfluoropolyethers). Fatty alcohols, fatty acids (stearic acid) and waxes beeswax, carnauba wax or paraffin wax may also be used as fats.

Exemplary emulsifiers according to the invention include glyceryl stearate, polysorbate 60 and the PEG-6/PEG-32/ glycol stearate mixture marketed under the trademark Tefose® 63 by Gattefosse.

Exemplary solvents accorrding to the invention include the lower alcohols, in particular ethanol and isopropanol, and propylene glycol.

Exemplary hydrophilic gelling agents which are suitable include carboxyvinyl polymers (carbomer), acrylic copolymers such as acrylate/alkylacrylate copolymers, polyacrylamides, polysaccharides such as hydroxypropyl cellulose, natural gums and clays, and, as lipophilic gelling agents, representative thereof are the modified clays such as bentones, fatty acid metal salts such as aluminum stearates, and hydrophobic silica, ethyl cellulose and polyethylene.

Exemplary hydrophilic active agents which may be incorporated include proteins or protein hydrolysates, amino acids, polyols, urea, allantoin, sugars and sugar derivatives, water-soluble vitamins, starch and plant extracts, in particular those of Aloe vera.

And exemplary lipophilic active agents include retinol (vitamin A) and derivatives thereof, tocopherol (vitamin E) and derivatives thereof, essential fatty acids, ceramides and essential oils.

It is also intended, inter alia, to combine the CGRP antagonists with active agents intended in particular for the prevention and/or treatment of skin conditions, complaints and afflictions. Exemplary of these active agents are:

(1) Agents which modify cutaneous differentiation and/or proliferation and/or pigmentation such as retinoic acid and isomers thereof, retinol and esters thereof, vitamin D and derivatives thereof, estrogens such as estradiol, kojic acid or hydroquinone;

(2) Antibacterial agents such as clindamycin phosphate, erythromycin or antibiotics from the tetracycline family;

(3) Antiparasitic agents, in particular metronidazole, crotamiton or pyrethroids;

(4) Antifungal agents, in particular compounds of the imidazole family such as econazole, ketoconazole or miconazole or salts thereof, polyene compounds such as amphotericin B, compounds of the allylamine family such as terbinafine, or alternatively octopirox;

(5) Steroidal anti-inflammatory agents such as hydrocortisone, betamethasone valerate or clobetasol propionate, or nonsteroidal anti-inflammatory agents such as ibuprofen and salts thereof, diclofenac and salts thereof, acetylsalicylic acid, acetaminophen or glycyrrhetinic acid;

(6) Anaesthetics such as lidocaine hydrochloride and derivatives thereof;

(7) Antipruriginous agents such as thenaldine, trimeprazine or cyproheptadine;

(8) Antiviral agents such as acyclovir;

(9) Keratolytic agents such as alpha- and beta-hydroxycarboxylic acids or beta-ketocarboxylic acids, the salts, amides or esters thereof and more particularly hydroxy acids such as glycolic acid, lactic acid, salicylic acid, citric acid and fruit acids in general, and 5-n-octanoylsalicylic acid;

(10) Anti-free-radical agents such as alpha-tocopherol or esters thereof, superoxide dismutases, certain metal chelating agents or ascorbic acid and esters thereof;

(11) Antiseborrhoeic agents such as progesterone;

(12) Antidandruff agents such as octopirox or zinc pyrithione;

(13) Antiacne agents such as retinoic acid or benzoyl peroxide.

Advantageously, the CGRP antagonists are combined with compounds or species, and in particular active agents normally eliciting an irritant side effect, and, especially, active agents used conventionally in the cosmetic, pharmaceutical or dermatological field. The presence of a CGRP antagonist in a cosmetic, pharmaceutical or dermatological composition containing an active agent exhibiting an irritant effect makes it possible to attenuate this irritant effect greatly, or even to eliminate it altogether.

In particular, the CGRP antagonists permit increasing the amount of cosmetic, pharmaceutical or dermatological active agent relative to the amount normally employed, for the purpose of improved efficacy.

Thus, the present invention also features topically applicable compositions containing a cosmetically, pharmaceutically or dermatologically acceptable medium and at least one active agent exhibiting an irritant side effect, and also comprising at least one CGRP antagonist.

The irritants according to the invention include, in particular, fragrances, surfactants (ionic or nonionic surfactants), preservatives, certain sunscreens, organic solvents, alcoholic solutions and certain cosmetic, pharmaceutical or dermatological active agents.

In particular, the active agents exhibiting an irritant side effect are selected from among α-hydroxy acids (glycolic acid, lactic acid, malic acid, citric acid, tartaric acid and mandelic acid), β-hydroxy acids (salicylic acid and derivatives thereof), α-keto acids, β-keto acids, retinoids (retinol and esters thereof, retinal, retinoic acid and derivatives thereof, and retinoids, in particular those described in FR-A-2,570,377, EP-A-199,636, EP-A-325,540 and EP-A-402, 072), anthralins (dioxyanthranol), anthranoids, peroxides, minoxidil, lithium salts, antimetabolites, vitamin D and derivatives thereof, hair dyes or colorants (paraphenylenediamine and derivatives thereof, and aminophenols), perfumed alcoholic solutions (perfumes, eaux de toilette, aftershave and deodorants), antiperspirants (certain aluminum salts), depilatory or permanent-waving active agents (thiols), depigmenting agents (hydroquinone) and anti-lice active agents (pyrethrin).

The use of a CGRP antagonist makes it possible, in particular, to amplify the amount of product, and more especially of active agent exhibiting an irritant side effect, by 2 to 10 times compared with the state of the art, without experiencing the aforesaid discomforts. Thus, it is possible to formulate the hydroxy acids at up to 50% of the weight of the composition, or the retinoids at up to 5%, without any discomfort.

The present invention also features a cosmetic treatment, comprising topically applying a composition as described above, containing at least one CGRP antagonist in a cosmetically acceptable medium, to the skin, to the scalp and/or to the mucous membranes.

The cosmetic treatment of the invention may be carried out, in particular, by applying the cosmetic or hygiene compositions as described above, via the usual technique for applying these compositions. For example: application of creams, gels, sera, lotions, makeup-removing milks or after-sun compositions to the skin or to dry hair, application of a hair lotion to wet hair, application of shampoo, or alternatively application of toothpaste to the gums.

In order to further illustrate the present invention and the advantages thereof, the following specific examples are given, it being understood that same are intended only as illustrative and in nowise limitative.

In said examples to follow, all parts and percentages are given by weight.

EXAMPLE 1:

Makeup-removing lotion for the face:

| | |
|---|---|
| CGRP 8–37 | 0.50 |
| Antioxidant | 0.05 |
| Isopropanol | 40.00 |
| Preservative | 0.30 |
| Water qs | 100% |

EXAMPLE 2:

Makeup-removing lotion for the face:

| | |
|---|---|
| CGRP 8–37 | 0.0001 |
| Antioxidant | 0.05 |
| Isopropanol | 40.00 |
| Preservative | 0.30 |
| Water qs | 100% |

EXAMPLE 3:

Facial care gel:

| | |
|---|---|
| Anti-CGRP antibody | 0.05 |
| Hydroxypropyl cellulose (Klucel H marketed by Hercules) | 1.00 |
| Antioxidant | 0.05 |
| Isopropanol | 40.00 |
| Preservative | 0.30 |
| Water qs | 100% |

EXAMPLE 4:

Acne treatment gel:

| | |
|---|---|
| Anti-CGRP antibody | 0.10 |
| all-trans-Retinoic acid | 0.05 |
| Hydroxypropyl cellulose (Klucel H marketed by Hercules) | 1.00 |
| Antioxidant | 0.05 |
| Isopropanol | 40.00 |
| Preservative | 0.30 |
| Water qs | 100% |

EXAMPLE 5:

Facial care cream (oil-in-water emulsion):

| | |
|---|---|
| CGRP 8–37 | 0.02 |
| Glyceryl stearate | 2.00 |
| Polysorbate 60 (Tween 60 marketed by ICI) | 1.00 |
| Stearic acid | 1.40 |
| Triethanolamine | 0.70 |
| Carbomer | 0.40 |
| Liquid fraction of karite butter | 12.00 |
| Perhydrosqualene | 12.00 |
| Antioxidant | 0.05 |
| Fragrance | 0.5 |
| Preservative | 0.30 |
| Water qs | 100% |

EXAMPLE 6:

Shampoo:

| | |
|---|---|
| Sodium lauryl ether sulfate (2.2 EO) | 12.00 |
| Anti-CGRP antibody | 0.02 |
| Hydroxypropyl cellulose (Klucel H marketed by Hercules) | 1.00 |
| Fragrance | 0.50 |
| Preservative | 0.30 |
| Water qs | 100% |

EXAMPLE 7:

Facial anti-wrinkle care cream (oil-in-water emulsion):

| | |
|---|---|
| CGRP 8–37 | 0.15 |
| Glyceryl stearate | 2.00 |
| Polysorbate 60 (Tween 60 marketed by ICI) | 1.00 |
| Stearic acid | 1.40 |
| 5-n-Octanoylsalicylic acid | 0.50 |
| Triethanolamine | 0.70 |
| Carbomer | 0.40 |
| Liquid fraction of karite butter | 12.00 |
| Perhydrosqualene | 12.00 |
| Antioxidant | 0.05 |
| Fragrance | 0.5 |
| Preservative | 0.30 |
| Water qs | 100% |

EXAMPLE 8:

Emulsified care gel for countering insect bites (oil-in-water emulsion):

| | |
|---|---|
| Cyclomethicone | 3.00 |
| Purcellin oil (marketed by Dragoco) | 7.00 |
| PEG-6/PET-32/glycol stearate (Tefose ® 63 marketed by Gattefosse) | 0.30 |
| Anti-CGRP antibody | 0.02 |
| Preservative | 0.30 |
| Fragrance | 0.40 |
| Carbomer | 0.60 |
| Crotamiton | 5.00 |
| Glycyrrhetinic acid | 2.00 |
| Ethyl alcohol | 5.00 |
| Triethanolamine | 0.20 |
| Water qs | 100% |

EXAMPLE 9:

Pain-relief gel:

| | |
|---|---|
| CGRP 8–37 | 0.03 |

-continued

| Hydroxypropyl cellulose (Klucel H marketed by Hercules) | 1.00 |
|---|---|
| Antioxidant | 0.05 |
| Lidocaine hydrochloride | 2.00 |
| Isopropanol | 40.00 |
| Preservative | 0.30 |
| Water qs | 100% |

EXAMPLE 10:

Care cream for facial rosacea (oil-in-water emulsion):

| CGRP 8–37 | 0.25 |
|---|---|
| Glyceryl stearate | 2.00 |
| Polysorbate 60 (Tween 60 marketed by ICI) | 1.00 |
| Stearic acid | 1.40 |
| Metronidazole | 1.00 |
| Triethanolamine | 0.70 |
| Carbomer | 0.40 |
| Liquid fraction of karite butter | 12.00 |
| Liquid petrolatum | 12.00 |
| Antioxidant | 0.05 |
| Fragrance | 0.50 |
| Preservative | 0.30 |
| Water qs | 100% |

EXAMPLE 11:

Care cream for solar erythema (oil-in-water emulsion):

| Anti-CGRP antibody | 0.25 |
|---|---|
| Glyceryl stearate | 2.00 |
| Polysorbate 60 (Tween 60 marketed by ICI) | 1.00 |
| Stearic acid | 1.40 |
| Glycyrrhetinic acid | 2.00 |
| Triethanolamine | 0.70 |
| Carbomer | 0.40 |
| Liquid fraction of karite butter | 12.00 |
| Sunflower oil | 10.00 |
| Antioxidant | 0.05 |
| Fragrance | 0.50 |
| Preservative | 0.30 |
| Water qs | 100% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable therapeutic/cosmetic composition adopted for the therapeutic treatment or care of sensitive human skin, mucous membranes, and/or the scalp, comprising an effective therapeutically/cosmetically effective amount of at least one calcitonin gene related peptide (CGRP) antagonist and a therapeutically/cosmetically acceptable vehicle, diluent or carrier therefor, and which further comprises at least one normally skin-irritating bioactive agent, and wherein the relative ratio of the amounts of said CGRP antagonist to said bioactive agent in said composition are such that the irritation normally associated with said bioactive agent upon topical application to sensitive skin is inhibited or prevented by said CGRP antagonist.

2. The therapeutic/cosmetic composition as defined by claim 1, said at least one CGRP antagonist comprising CGRP 8-37 or an anti-CGRP antibody.

3. The therapeutic/cosmetic composition as defined by claim 1, said at least one CGRP antagonist comprising from 0.000001% to 10% by weight thereof.

4. The therapeutic/cosmetic composition as defined by claim 3, said at least one CGRP antagonist comprising from 0.0001% to 5% by weight thereof.

5. The therapeutic/cosmetic composition as defined by claim 1, which is in the form selected from the group consisting of a solution, emulsion, milk, lotion, microemulsion, gel, serum, cream, mousse, soap, shampoo, aerosol, dispersion, microcapsules, and microparticles.

6. The therapeutic/cosmetic composition as defined by claim 1, wherein the skin-irritating agent is selected from the group consisting at least one antibacterial agent, antiparasitic agent, antifungal agent, anti-inflammatory agent, anti-pruriginous agent, anaesthetic, antiviral agent, keratolytic agent, anti-free-radical agent, antiseborrhoeric agent, anti-dandruff agent, antiacne agent, and agent that modifies the differentiation and/or proliferation and/or pigmentation of human skin.

7. The therapeutic/cosmetic composition as defined by claim 6, wherein the compostion further comprises another agent selected from the group consisting of lidocaine hydrochloride, an antiparasitic agent and a non-steroidal anti-inflammatory.

8. The therapeutic/cosmetic composition as defined by claim 1, said at least one normally skin-irritating bioactive agent selected from the group consisting of a fragrance, a surfactant, a preservative, a sunscreen, an organic solvent, and an alcohol.

9. The therapeutic/cosmetic composition as defined by claim 1, said at least one normally skin-irritating bioactive agent selected from the group consisting of an α-hydroxy acid, a β-hydroxy acid, an α-keto acid, a β-keto acid, a retinoid, an anthralin, an anthranoid, a peroxide, minoxidil, a lithium salt, an antimetabolite, vitamin D or derivative thereof, a hair dye or colorant, an alcoholic perfume, an antiperspirant, a depilatory, a permanent-waving active agent, a depigmenting active agent, and an anti-lice active agent.

10. The therapeutic/cosmetic composition as defined by claim 9, said at least one normally skin-irritating bioactive agent comprising an α-hydroxy acid.

11. A regime for therapeutically preventing and/or combating skin irritations and/or dartres and/or erythema and/or dysaesthetic sensations and/or sensations of inflammation and/or pruritis of human skin, scalp, and/or the mucous membranes, comprising topically applying thereto, for such period of time as is required to elicit the desired preventative or therapeutic response, a therapeutically/cosmetically effective amount of at least one CGRP antagonist.

12. A regime for therapeutically preventing and/or combating skin irritations and/or dartres and/or erythema and/or dysaesthetic sensations and/or sensations of inflammation and/or pruritis of human skin, hair, scalp, nails and/or the mucous membranes, comprising topically applying thereto, for such period of time as is required to elicit the desired preventative or therapeutic response, a therapeutically/cosmetically effective amount of the therapeutic/cosmetic composition as defined by claim 1.

13. A regime for therapeutically preventing and/or combating skin irritations and/or dartres and/or erythema and/or dysaesthetic sensations and/or sensations of inflammation and/or pruritis of human skin, scalp, and/or the mucous membranes, comprising topically applying thereto, for such period of time as is required to elicit the desired preventative or therapeutic response, a therapeutically/cosmetically effective amount of the therapeutic/cosmetic composition as defined by claim 9.

* * * * *

UNITED STATES PATENT AND TRADEMARK OFFICE
CERTIFICATE OF CORRECTION

PATENT NO.    : 6,019,967
DATED         : February 1, 2000
INVENTOR(S)   : Lionel Breton et al.

Page 1 of 1

It is certified that error appears in the above-identified patent and that said Letters Patent is hereby corrected as shown below:

Column 3,
Line 52, please change "induce an" to -- reduce --.

Signed and Sealed this

Twenty-eighth Day of August, 2001

Attest:

*Attesting Officer*

NICHOLAS P. GODICI
*Acting Director of the United States Patent and Trademark Office*